US006306845B1

(12) United States Patent
Butler, Jr.

(10) Patent No.: US 6,306,845 B1
(45) Date of Patent: Oct. 23, 2001

(54) METHOD FOR TREATING DEMYELINATING DISEASE

(75) Inventor: Vincent P. Butler, Jr., New York, NY (US)

(73) Assignee: The Trustees of Columbia University in the City of New York, New York, NY (US)

( * ) Notice: Subject to any disclaimer, the term of this patent is extended or adjusted under 35 U.S.C. 154(b) by 0 days.

(21) Appl. No.: 09/240,935

(22) Filed: Jan. 29, 1999

(51) Int. Cl.$^7$ .................. A61K 31/58; A61K 31/585; C07T 540/105; A61F 2/00; A61L 9/04
(52) U.S. Cl. .................. 514/172; 514/172; 514/175; 514/824; 514/903; 540/105; 424/422; 424/423; 424/424; 424/45; 424/434; 424/436; 424/437; 424/158.1
(58) Field of Search ..................... 424/434, 422, 424/45, 427, 423, 437, 436, 158.1; 540/105; 514/172, 175, 824, 903

(56) References Cited

U.S. PATENT DOCUMENTS 3,857,832 * 12/1974 Hartenstein et al. ............. 260/210.5

OTHER PUBLICATIONS

ACS, RN 508–52–1, CN Ouabain genin, Ouabagenin, 1999.*
Chen, K.K., Henderson, F.G., and Anderson, R.C., (1950) "The cardiac action of Helleborus glycosides and their aglycones", *J. Pharmacol Exp. Ther.*, 99:395–400 (Exhibit 1).
Chen, K.K., and Henderson, F.G., (1954) "Pharmacology of sixty–four cardiac glycosides and aglycones", *J. Pharmacol Exp. Ther.*, 111:365–383 (Exhibit 2).
Chen, K.K., Jensen, H., and Chen, A.L. (1931) "Action of bufagins isolated from different species of toads", *Proc Soc Exp Biol Med.*, 29:905–906, (Exhibit 3).
Chen, K.K., Robbins, E.B., and Worth, H., (1938) "The significance of the sugar component in the molecule of cardiac glycosides", *J. Am Pharmaceut Assn*, 27:189–195 (Exhibit 4).
Fieser, L.F., and Fieser, M., (1959) "Steroids", *Reinhold Pub. Corp., New York*, 727–809 (Exhibit 5).
Fink, B.R. and Cairns, A.M., (1983) "A new approach to differential peripheral nerve fiber block: Na$^+$, K$^+$–ATPase inhibition", *Anesthesiology* 59:127–131, (Exhibit 6).

Kaji, R., Happel, L. and Sumner, A.J., (1990) "Effect of digitalis on clinical symptoms and conduction variables in patients with multiple sclerosis", *Ann Neurol*, 28:582–584, (Exhibit 7).
Kaji, R. and Sumner, A.J., (1989) "Effect of digitals on central demyelinative conduction block in vivo", *Ann Neurol*, 25:159–165, (Exhibit 8).
Kaji, R. and Sumner, A.J., (1989) "Ouabain reverse conduction disturbances in single demyelinated nerve fibers", *Neurology*, 39:1364–1368, (Exhibit 9).
Kimura, J., (1996) "Consequences of peripheral nerve demyelination: basic and clinical aspects", *Brain Res*, 619:278–290, (Exhibit 10).
Kutemeier, P. and Danos, E.A., (1992) "Digoxin in mulitple sclerosis", *Ann Pharmacother*, 26:500–501, (Exhibit 11).
Nezu, A., et al., (1996) "Effect of digitalis on conduction dysfunction in Pelizaeus–Merzbacher diseasel", *J Neurol Sci*, 141:49–52, (Exhibit 12).
Shrager, P., (1993) "Axonal coding of action potentials in demyelinated nerve fibers", *Brain Res*, 619:278–290, (Exhibit 13).
Shimuzu, S., (1916) "Pharmacological and chemical studies on "Senso", the dried venom of the Chinese toad", *J Pharmacol Exp Ther*, 8:347–383, (Exhibit 14).
Sivam, S.P., et al., (1982) "Interaction of ouabain and propranolol in the central nervous system", *Pharmacology*, 25:286–293 (Exhibit 15).
Steyn, P.S. and van Heerden, F.R., (1998) "Bufadienolides of plant and animal origin", *Natural Prod Rep..* 397–413, (Exhibit 16).
Taylor, C.A., Tsai, C. and Lehmann, J., (1988) "Sodium fluxes modulating neuronal glutamate uptake: differential effects of local anesthetic and anticonvulsant drugs", *J Pharm & Exp Ther*, 255:666–673, (Exhibit 17).
Thomas, R., Gray, P., and Andrews, J., (1990) "Digitalis: its mode of action, receptor, and structure–activity relationships", *Adv. Drug Res.*, 19:311–562 (Exhibit 18); and Yoshida, S. Kamano, Y., and Saki, T., (1976) "Studies on the surface anesthetic activity of bufadienolides isloated from Chan Su", *Chem Pharm Bull*, 24:1741–1717 (Exhibit 19).

* cited by examiner

*Primary Examiner*—Sabiha Qazi
(74) *Attorney, Agent, or Firm*—John P. White; Cooper & Dunham LLP

(57) ABSTRACT

The present invention provides a method for treating a demyelinating disease in a subject which includes administering to the subject a therapeutically effective amount of a high affinity neuromodulatory Na,K-ATPase so as to treat the demyelinating disease.

15 Claims, No Drawings

METHOD FOR TREATING DEMYELINATING DISEASE

Throughout this application, various publications are referred to by arabic numeral within parentheses. Full citations for these publications are presented immediately before the claims. Disclosures of these publications in their entireties are hereby incorporated by reference into this application in order too more fully describe the state of the art to which this invention pertains.

BACKGROUND OF THE INVENTION

The digitalis glycosides, which are so well known because they have been widely used clinically for more than two centuries, are representatives of a much larger group of potent and specific steroidal inhibitors of Na,K-ATPase. The Na,K-ATPase inhibitory moieties of these compounds all belong to one of two structurally related, yet distinct, families of compounds: cardenolides and bufadienolides. Cardenolides and bufadienolides both possess similar steroidal structures, which are somewhat unusual among naturally occurring compounds in that their C and D rings are oriented in a cis configuration. Cardenolides differ structurally from bufadienolides only in that the lactone ring linked to the C17 position on the D ring of cardenolides is a five-membered γ lactone ring, while the lactone ring of bufadienolides is a six-membered δ lactone ring. The importance of the lactone ring is underscored by the fact that unconjugated bufadienolides with δ lactone rings are approximately tenfold more potent as Na,K-ATPase inhibitors than unconjugated cardenolides with identical steroidal structures, but with γ lactone rings.

Both cardenolides and bufadienolides found widely distributed throughout the plant and animal kingdoms and are almost invariably in the form of C3 conjugates, principally glycosides and esters. Toad conjugates differ from plant conjugates in that they are conjugated to arginyl hemisuberate residues rather than sugar residues. A very striking feature of all of these conjugates is the fact that, in the species in which they are most abundant (*Digitalis, Scilla* [squill], dozens of other plants, certain insects, bufonid toads, and *Rhabdophis tigrinus*, a snake), the steroidal molecules and their conjugates are quite heterogeneous, with dozens of molecular species often present. Plant conjugates (of both bufadienolides and cardenolides) are glycosides, while toad conjugates most commonly are carboxyl esters. The best characterized toad carboxyl esters are the arginyl suberate esters of toad bufadienolides, which are abundant in toad skin and cutaneous glandular secretions (11), and which are known as bufotoxins; small amounts of similar arginyl suberate esters of cardenolides ("cardenobufotoxins") have also been described in toad skin and cutaneous secretions.

Unconjugated bufadienolides and cardenolides are sometimes referred to as genins or, alternatively, when derived from plant glycosides, they may be referred to as aglycones. The active steroid components of bufotoxins are also referred to as genins. The cardiac genins are the active moieties of cardiac glycosides. The cardiac glycosides are a large group of sugar conjugates of cardiotonic steroids derived from a variety of plant sources including Digitalis, Strophanthus, Convallaria, Scilla and Helleborus. Except for the unconjugated bufadienolides which are often present in appreciable amounts in toad cutaneous glandular secretions, genins are rarely present as major components of fresh specimens obtained from plants, toads, or insects. Toad bufotoxins and plant bufadienolide glycosides are usually comparable in Na,K-ATPase inhibitory potency with corresponding bufadienolide genins; on the other hand, cardenolide glycosides are generally at least one order of magnitude more effective as Na,K-ATPase inhibitors than are their corresponding cardenolide genins.

The neural effects of digitalis and related compounds have been appreciated for most of this century and there is considerable recent evidence to suggest that many of the beneficial effects of digitalis in congestive heart failure are neurally mediated. It is also known that ouabain, injected into a nerve can cause nerve block (2) and that several bufadienolide genins are effective topical anesthetics (1,9,12,16). However, there have been relatively few experimental efforts to explore the potential therapeutic neural effects of systemic digitalis administration in noncardiac disease. It has been generally thought that, because of the relatively poor penetrance of the blood-brain barrier (BBB) by clinically available glycosides, therapeutically acceptable doses of these glycosides would not exert clinically significant neural effects. Cardenolide and bufadienolide genins, which readily cross the BBB, have rarely been used clinically, even though their neural-to-myocardial tissue concentration ratio is such that one can theoretically achieve a five-to ten-fold increase in CNS levels while halving the myocardial concentration. Reluctance to employ genins presumably stems from the fact that the aglycones (genins) of the clinically used digitalis glycosides are only about one tenth as potent as the corresponding glycosides. Since, until recently, most physicians believed that much of the beneficial clinical effect of digitalis stemmed from its direct myocardial actions, there was an understandable belief that less potent, but potentially neurotoxic agents, would have limited, it any, clinical utility.

The action of cardiac glycosides and genins on nerve conduction has been studied in experimental animals. Ouabain, injected into a nerve, can cause nerve block (2). Several bufadienolide genins have been shown to be effective as topical anesthetics (1,9,12,16).

Additionally, during the past decade, several reports have appeared, providing evidence that, by virtue of its ability to inhibit Na,K-ATPase, ouabain, an especially polar glycoside, can enhance neural conduction in several experimental models of demyelination (4,5,6,10,14), presumably by lowering the resting potential of hyperpolarized, demyelinated neurons (via inhibition of the sodium-potassium pump, or Na,K-ATPase). The less polar cardenolide glycoside, digoxin, has been given to seven patients with multiple sclerosis and to three patients with Pelizaeus-Merzbacher disease. Slight improvement in symptoms and in neurophysiological measurements were noted in six of the ten patients (3,8). It was noted that the effects were limited by dosage constraints (related to the risk of cardiac arrhythmias) and by limited passage of digoxin across the blood brain barrier (3,8,7).

Both the bufadienolide glycosides and the cardenolide glycosides (mainly, the latter) have been used extensively for more than sixty years in the treatment of congestive heart failure and certain cardiac arrhythmias.

There are no records of plant bufadienolide genins being used clinically, or of cardenolide genins used therapeutically in humans, nor of cardiac genins used in treatment of neurological disease. A toad bufadienolide genin (cinobufagin) was administered to patients with atrial fibrillation. Intravenous doses of 1 mg rapidly slowed the heart rate of some patients, but the effect was dissipated within five hours (indicating a much shorter time of action than digoxin or digitoxin, which are administered only once daily). Doses of 2–4 mg were toxic (nausea and vomiting). There is no evidence that cinobufagin can take the place of digitalis.

SUMMARY OF THE INVENTION

The present invention provides a method for treating a demyelinating disease in a subject which comprises administering to the subject a therapeutically effective amount of a cardiac genin so as to treat the demyelinating disease.

DETAILED DESCRIPTION OF THE INVENTION

This invention provides a method for treating a demyelinating disease in a subject which comprises administering to the subject a therapeutically effective amount of a cardiac genin so as to treat the demyelinating disease. The presently preferred high affinity neuromodulatory Na,K-ATPase inhibitor is a cardiac genin.

In an embodiment of this invention the cardiac genin is an unconjugated bufadienolide. In another embodiment of this invention, the cardiac genin is a cardenolide. In an embodiment of the invention the cardiac genin is the active moiety of the cardiac glycosides.

The present invention provides a method wherein the cardiac genin has the structure:

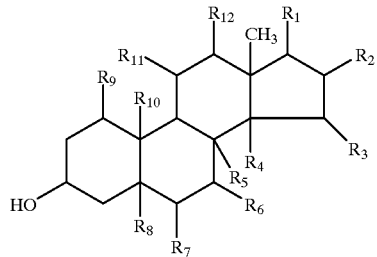

wherein the compound is (+) or (−);
$R_1$ is 2-pyrone or 2-furanone;
$R_2$ and $R_7$ are each independent H, OH or $OCOCH_3$;
$R_3$ is H or together with $R_4$ forms an epoxide ring;
$R_4$ is OH, or together with $R_3$ forms an epoxide ring;
$R_5$ is H, OH, or together with $R_6$ forms an epoxide ring;
$R_6$ is H, OH or together with $R_5$ forms an epoxide ring;
$R_8$, $R_9$ and $R_{11}$ are each independently H or OH;
$R_{10}$ is $HCO_3$, $CH_3$, CHO, or $CH_2OH$;
$R_{12}$ is H, OH or =O;
or a pharmaceutically acceptable salt or ester thereof.

In another embodiment, the present invention provides a method wherein the cardiac genin has the structure:

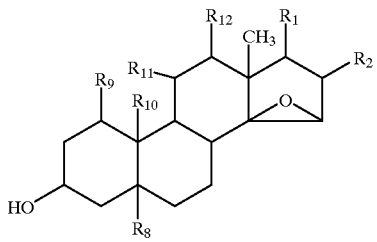

wherein
the compound is (+) or (−);
$R_1$ is 2-pyrone or 2-furanone;
$R_2$ is H, OH or $OCOCH_3$;
$R_8$, $R_9$ and $R_{11}$ are each independently H or OH;
$R_{10}$ is $HCO_3$, $CH_3$, CHO, or $CH_2OH$;
$R_{12}$ is H, OH or =O;
or a pharmaceutically acceptable salt or ester thereof.

The present invention also provides a method wherein the cardiac genin has the structure:

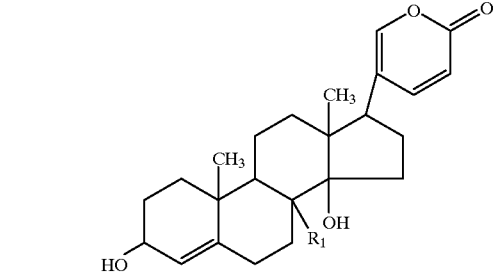

wherein
the compound is (+) or (−);
$R_1$ is 2-pyrone or 2-furanone;
$R_{11}$ is H or OH;
$R_{12}$ is H, OH or =O;
or a pharmaceutically acceptable salt or ester thereof.

This invention provides a method wherein the cardiac genin has the structure:

wherein $R_1$ is H or OH or a pharmaceutically acceptable salt or ester thereof.

In one embodiment of this invention the cardiac genin is derived from a plant. In another embodiment of this invention the cardiac genin is derived from an animal source. In another embodiment, the cardiac genin is synthesized.

The present invention provides a method for treating demyelinating disease in a subject comprising administering to the subject an amount of the pharmaceutical composition disclosed herein, effective to treat the demyelinating disease in the subject. According to an embodiment of this invention, the demyelinating disease is multiple sclerosis, spinal cord compression, ischemia, acute disseminated encephalomyelitis, optic neuromyelitis, adrenoleukodystrophy, progressive multifocal leukoencephalopathy, metabolic disorders, toxic exposure, congenital demylinating disease or peripheral neuropathy.

The present invention relates to demyelinating disease and sequences which correspond to and are implicated in the development of the demyelinating disease including neuronal damage or damage to the myelin sheath.

The present invention provides a pharmaceutical composition comprising a pharmaceutically acceptable carrier and a therapeutically effective amount of a cardiac genin.

In the practice of any of the methods of the invention or preparation of any of the pharmaceutical compositions an "therapeutically effective amount" is an amount which is capable of treating the demyelinating disease. Accordingly, the effective amount will vary with the subject being treated, as well as the condition to be treated. Such factors would be determined by one skilled in the art. For the purposes of this invention, the methods of administration are to include, but are not limited to, administration cutaneously, subcutaneously, intravenously, orally, topically, by aerosol, by epidural, intraperitoneal injection, intramuscular injection, nasally, anally, or by ocular or otic delivery.

In the present invention the therapeutically effective amount comprises a dose from about 0.01 mg/kg/day to about 10 mg/kg/day. In one embodiment the therapeutically effective amount comprises a dose from about 0.4 mg/kg/day to about 6.0 mg/kg/day. In another embodiment this invention provides a composition wherein the therapeutically effective amount comprises a concentration from about 0.01 mg/ml to about 1000 mg/ml. In another embodiment this invention provides a composition wherein the therapeutically effective amount comprises a concentration from about 1 mg/ml to about 100 mg/ml.

As used herein, the term "pharmaceutically acceptable carrier" encompasses any of the standard pharmaceutically accepted carriers, such as phosphate buffered saline solution, water, emulsions such as oil/water emulsion, alcohol elixir or a triglyceride emulsion, various types of wetting agents, tablets, coated tablets and capsules or transdermal patch.

When administered, compounds are often cleared rapidly from the circulation and may therefore elicit relatively short-lived pharmacological activity. Consequently, frequent injections or oral dosing of relatively large doses of bioactive compounds may be required to sustain therapeutic efficacy. Compounds modified by the covalent attachment of water-soluble polymers such as polyethylene glycol, copolymers of polyethylene glycol and polypropylene glycol, carboxymethyl cellulose, dextran, polyvinyl alcohol, polyvinylpyrrolidone or polyproline are known to exhibit substantially longer half-lives in blood following intravenous injection than do the corresponding unmodified compounds (Abuchowski, et al., 1981; Newmark et al., 1982; and Katre et al., 1987). Such modifications may also increase the compound's solubility in aqueous solution, eliminate aggregation, enhance the physical and chemical stability of the compound, and greatly reduce the immunogenicity and reactivity of the compound. As a result, the desired in vivo biological activity may be achieved by the administration of such polymer-compound adducts less frequently or in lower doses than with the unmodified compound.

In the practice of the method administration may comprise daily, weekly, monthly, hourly or by peak and trough, the precise frequency being subject to various variables such as age and condition of the subject, amount to be administered, half-life of the agent in the subject, area of the subject to which administration is desired and the like.

In connection with the method of this invention, a therapeutically effective amount may include dosages which take into account the size and weight of the subject, the age of the subject, the severity of the symptom, the stage of the demyelinating disease, the efficacy of the agent and the method of delivery of the agent. One of ordinary skill in the art would be readily able to determine the exact dosages and exact times of administration based upon such factors.

The present invention provides a composition having the structure:

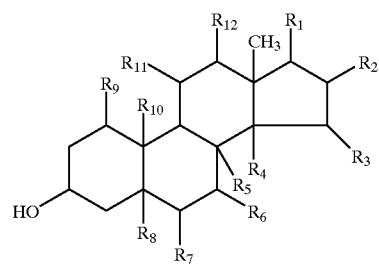

wherein the compound is (+) or (−);

$R_1$ is 2-pyrone or 2-furanone;

$R_2$ and $R_7$ are each independently H, OH or $OCOCH_3$;

$R_3$ is H or together with $R_4$ forms an epoxide ring;

$R_4$ is OH, or together with $R_3$ forms an epoxide ring;

$R_5$ is H, OH, or together with $R_6$ forms an epoxide ring;

$R_6$ is H, OH or together with $R_5$ forms an epoxide ring;

$R_8$, $R_9$ and $R_{11}$ are each independently H or OH;

$R_{10}$ is $HCO_3$, $CH_3$, CHO, or $CH_2OH$;

$R_{12}$ is H, OH or =O;

or a pharmaceutically acceptable salt or ester thereof.

The present invention also provides a composition having the structure:

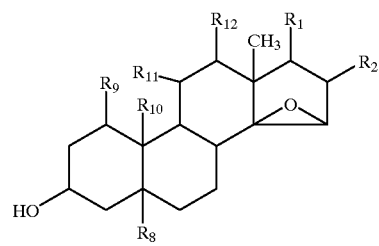

wherein the compound is (+) or (−);

$R_1$ is 2-pyrone or 2-furanone;

$R_2$ is H, OH or $OCOCH_3$;

$R_8$, $R_9$ and $R_{11}$ are each independently H or OH;

$R_{10}$ is $HCO_3$, $CH_3$, CHO, or $CH_2OH$;

$R_{12}$ is H, OH or =O;

or a pharmaceutically acceptable salt or ester thereof.

The present invention provides a composition having the structure:

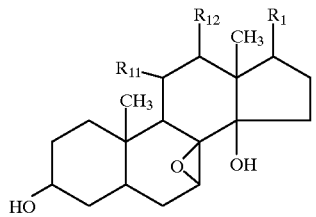

wherein
the compound is (+) or (−);
$R_1$ is 2-pyrone or 2-furanone;
$R_{11}$ is H or OH;
$R_{12}$ is H, OH or =O;
or a pharmaceutically acceptable salt or ester thereof.

The present invention also provides a composition having the structure:

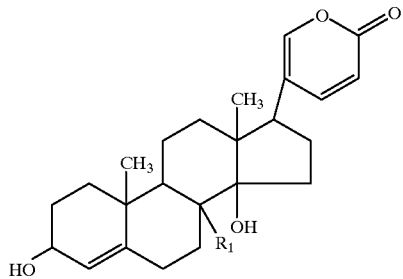

wherein $R_1$ is H or OH or a pharmaceutically acceptable salt or ester thereof.

The therapeutically effective amount for administration may include dosages that account for the size, weight and age of the subject as well as the severity of the demyelinating disease. Additional factors that may affect dosages include the efficacy of the agent and the method of delivery of the agent. Such factors would be well known to one skilled in the art. The exact dosages and times of administration would be determined by one skilled in the art.

The pharmaceutical composition contains a cardiac genin that consists of a steroid base containing a δ or γ-unsaturated lactone ring. The cardiac genin consisting of a δ lactone ring is a bufadienolide. The cardiac genin consisting of a γ lactone ring is a cardenolide. The pharmaceutical composition contains either bufadienolide cardiac genins or cardenolide cardiac genins.

In the practice of any of the methods of the invention or preparation of any of the pharmaceutical compositions a "therapeutically effective amount" is an amount which is capable of treating demyelinating disease. Accordingly, the effective amount will vary with the subject being treated, the way the pharmaceutical composition is metabolized, as well as the severity of the demyelinating disease in the subject. Such factors would be determined by one skilled in the art.

As used herein the term "pharmaceutically acceptable carrier" encompasses any of the standard pharmaceutically accepted carriers known to those of ordinary skill in the art useful in formulating pharmaceutical compositions and include but not limited to a liquid, solid, gel, or transdermal patch.

This invention will be better understood from the Experimental Details which follow. However, one skilled in the art will readily appreciate that the specific methods and results discussed are merely illustrative of the invention as described more fully in the claims which follow thereafter.

Experimental Details

Animal studies indicate that cardiac genins are more effective (as much as 20-fold more effective) than their corresponding glycosides in crossing the blood-brain barrier. This implies that if a genin is substituted for a glycoside, an equimolar dose of genin will exert 20 times more neural effects than the corresponding glycoside without any increase in the risk of cardiotoxicity. However, because of the risk of neurotoxicity, one would initiate a genin at one-twentieth the dosage of glycoside and progressively increase genin dosage as tolerated.

Cardiac genins, by virtue of their ability to cross the blood brain barrier and to inhibit neural Na K-ATPase, may be useful in the treatment of acute episodes of demyelination, particularly that due to multiple sclerosis of the relapsing remitting variety or in the acute phase of demyelination due to spinal cord compression or in cases of peripheral neuropathy.

Materials and Methods

In this study the effect of a plant bufadienolide, scillarenin, on a murine model of human multiple sclerosis, viz., experimental allergic encephalomyelitis (EAE) was performed. Scillarenin was prepared from proscillaridin by treatment with naringinase, a rhamnosidase.

A murine model of multiple sclerosis consists of inducing severe paralysis on mice for five to seven days using the experimental allergic encephalomyelitis (EAE) model. After seven days mice recover from the induced paralysis.

The cardiac genin scillarenin prepared from commercially available proscillaridin was administered to a group of control mice and prepared mice (EAE model). The dosage administered was in various concentrations of 0.4 to 6.0 mg/kg/day.

EAE is induced in eight to ten-week-old mice by a single subcutaneous flank injection of 100 µg of the acetylated N-terminal nonapeptide of mouse myelin basic protein in complete Freund's adjuvant, followed by the intravenous injection, 24 and 72 hours later, of 0.1 µg pertussis toxin. Mice are evaluated daily for signs of EAE on a scale of 0 to 5: 0, no signs; 1, tail weakness; 2 mild rear limb paresis; 3, severe rear limb paresis; 4, complete paralysis of rear limbs or of both limbs on one side; and 5, death.

Beginning 3 days after the onset of neurological manifestations, a scillarenin elixir is administered daily by gavage in 0.05 ml 95% ethanol (or in 0.1 ml 47.5% ethanol). Animals are observed for eight hours for amelioration of neurological deficits, using the scaling system described above.

Results

At a dose of 0.8 mg/kg/day, mice showed improvement for 6–8 hours after dosing (after the second dose). Within two hours of dosage, totally paralyzed hind limbs become largely functional. This point represents peak time for the cardiac genin effectiveness. Trough time is variable, depending on dosage and severity of paralysis.

A therapeutic response has been observed in animals receiving half the toxic dose, or in the range of 0.8 mg/kg. The use of high doses of scillarenin is related to the limited solubility of scillarenin and to the effectiveness of gavage. On studies of two two groups of mice (20 and 15 respectively), nine animals received what appears to be therapeutic doses of scillarenin for two or more days. Non-inclusion reflects many factors: neurotoxicity (convulsions, requiring sacrifice) with what is now recognized to be excessive doses; failure of the disease to progress to a scale of two or greater; the use of what was felt to be a subtherapeutic dose (5 mice in the first study); the need to include 5 control mice in both studies; inability to study some mice on two or more consecutive days.

The ethanol vehicle of the scillarenin gavage clearly had sedative effects. With the exception of one mouse, which showed slight improvement in leg motion on one occasion, improvement was not noted in any control animal receiving only the ethanol vehicle.

Of the nine mice receiving what was arbitrarily defined as a therapeutic dose, none exhibited a definite response on the first day. The nine treated mice could be divided into three groups based on their therapeutic responses on the second and third days. Three mice had no clear-cut response. Three had a definite response of 1 unit on the grading scale. The final three mice had extraordinary responses. Prior to scillarenin administration, two of these three mice had total paralysis of both rear extremities, and one had severe weakness. Within 2–3 hours, thes mice were walking, albeit with some difficulty, on all four extremities and did so for several hours until the end of a day's observation; by the next morning, they had relapsed to the pre-treatment state, but again had similar responses to scillarenin administration. The transitory nature of the response to scillarenin on two or three occasions lent strength to the response being drug induced. Prolonged studies were not possible because, after a few days, it was difficult to determine whether clinical improvement represented a therapeutic response or the spontaneous remission which occurs in the model of EAE.

References

1. Chen, K. K., Jensen, H., and Chen, A. L., (1931) "Action of bufagins isolated from different species of toads", *Proc Soc Exp Biol Med* 29:905–906,
2. Fink, B. R. and Cairns, A. M., (1983) "A new approach to differential peripheral nerve fiber block: $Na^+,K^+$-ATPase inhibition," *Anesthesiology* 59:127–131,
3. Kaji, R., Happel, L. and Sumner, A. J., (1990) "Effect of digitalis on clinical symptoms and conduction variables in patients with multiple sclerosis," *Ann Neurol* 28:582–584,
4. Kaji, R. and Sumner, A. J., (1989) "Effect of digitalis on central demyelinative conduction block in vivo," *Ann Neurol* 25:159–165,
5. Kaji, R. and Sumner, A. J., (1979) "Ouabain reverses conduction disturbances in single demyelinated nerve fibers," *Neurology* 39:1364–1368,
6. Kimura, J., (1996) "Consequences of peripheral nerve demyelination: basic and clinical aspects," *Brain Res* 619:278–290,
7. Kutemeier, P. and Danos, E. A., (1992) "Digoxin in multiple sclerosis," *Ann Pharmacother* 26:500–501,
8. Nezu, A., et al., (1996) "Effect of digitalis on conduction dysfunction in Pelizaeus-Merzbacher disease," *J Neurol Sci* 141:49–52,
9. Okada, M., (1966) "Pharmacology of the components of toad venom and allied substances," *Mem Inst Butnatan* 33:589–601,
10. Shrager, P., (1993) "Axonal coding of action potentials in demyelinated nerve fibers," *Brain Res* 619:278–290,
11. Shimada, K., et al., (1977) "Studies on cardiotonic steriods from the skin of Japanese toad," *Chem Pharm Bull* 25:714–730,
12. Shimuzu, S., (1916) "Pharmacological and chemical studies on "Senso," the dried venom of the Chinese toad," *J Pharmacol Exp Ther* 8:347–383,
13. Stanley, G. P. and Pender, P., (1991) "Consequences of peripheral nerve demyelination: basic and clinical aspects," *Can J Neurol Sci* 20:8800,
14. Yoshida, S., Kamano, Y. and Sakai, T.,(1976) "Studies on the surface anesthetic activity of bufadienolides isolated from Ch'an Su," *Chem Pharm Bull* 24:1741–1717.

What is claimed is:

1. A method for treating a demyelinating disease in a subject which comprises administering to the subject a therapeutically effective amount of a cardiac genin so as to treat the demyelinating disease, wherein the cardiac genin is a compound having the structure:

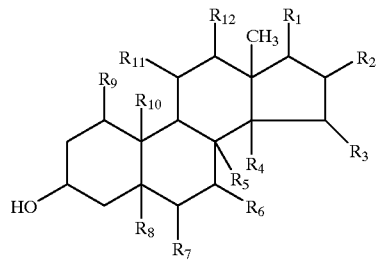

wherein
the compound is (+) or (−);
$R_1$ is 2-pyrone or 2-furanone;
$R_2$ and $R_7$ are each independently H, OH or $OCOCH_3$;
$R_3$ is H;
$R_4$ is OH;
$R_5$ is H, or OH;
$R_6$ is H, or OH;
$R_8$, $R_9$ and $R_{11}$ are each independently H or OH;
$R_{10}$ is $HCO_3$, $CH_3$, CHO, or $CH_2OH$;
$R_{12}$ is H, OH or =O;
or a pharmaceutically acceptable salt or ester thereof.

2. A method for treating a demyelinating disease in a subject which comprises administering to the subject a therapeutically effective amount of a cardiac genin so as to treat the demyelinating disease, wherein the cardiac genin has the structure:

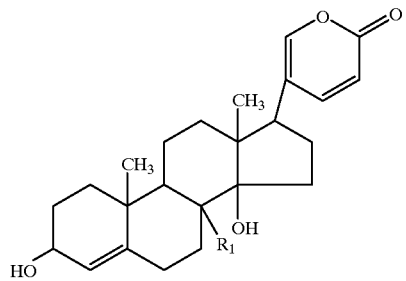

wherein $R_1$ is H or OH or a pharmaceutically acceptable salt or ester thereof.

3. The method of claim 1, wherein the cardiac genin is derived from a plant source.

4. The method of claim 1, wherein the cardiac genin is derived from an animal source.

5. The method of claim 1, wherein the cardiac genin is derived synthetically.

6. The method of claim 2, wherein the demyelinating disease is multiple sclerosis, spinal cord compression, ischemia, acute disseminated encephalomyelitis, optic neuromyelitis, adrenoleukodystrophy, progressive multifocal leukoencephalopathy, metabolic disorders, toxic exposure, congenital demyelinating disease or peripheral neuropathy.

7. The method of claim 2, wherein the demyelinating disease is multiple sclerosis.

8. The method of claim 2, wherein the demyelinating disease is neuronal damage or damage to the myelin sheath.

9. The method of claim 2, wherein administration comprises epidural, intraperitoneal, intramuscular, cutaneously, subcutaneous or intravenous injection, by aerosol, infusion, or topical, nasal, oral, anal, ocular or otic delivery.

10. The method of claim 2, wherein the therapeutically effective amount comprises a dose from about 0.01 mg/kg/day to about 10 mg/kg/day.

11. The method of claim 2, wherein the therapeutically effective amount comprises a dose from about 0.4 mg/kg/day to about 6.0 mg/kg/day.

12. The method of claim 2, wherein the therapeutically effective amount comprises a concentration from about 0.01 mg/ml to about 1000 mg/ml.

13. The method of claim 2, wherein the therapeutically effective amount comprises a concentration from about 1 mg/ml to about 100 mg/ml.

14. The method of claim 2, wherein the therapeutically effective amount of the cardiac genin comprises a pharmaceutically acceptable carrier.

15. The method of claim 14, wherein the pharmaceutically acceptable carrier comprises a liquid, solid, gel, or transdermal patch.

* * * * *